US008158366B2

(12) United States Patent
Samoylova et al.

(10) Patent No.: US 8,158,366 B2
(45) Date of Patent: *Apr. 17, 2012

(54) METHODS OF IDENTIFYING PEPTIDES AND COMPOSITIONS THAT BIND TO OOCYTES IN A SPECIES-SPECIFIC MANNER

(75) Inventors: Tatiana I. Samoylova, Auburn, AL (US); Henry J. Baker, Auburn, AL (US); Nancy Cox, Auburn, AL (US); Stephen Ditchkoff, Auburn, AL (US)

(73) Assignee: Auburn University, Auburn, AL (US)

( * ) Notice: Subject to any disclaimer, the term of this patent is extended or adjusted under 35 U.S.C. 154(b) by 107 days.

This patent is subject to a terminal disclaimer.

(21) Appl. No.: 12/419,883

(22) Filed: Apr. 7, 2009

(65) Prior Publication Data

US 2011/0044989 A1 Feb. 24, 2011

Related U.S. Application Data

(60) Provisional application No. 61/123,275, filed on Apr. 7, 2008, provisional application No. 61/130,473, filed on May 30, 2008, provisional application No. 61/133,201, filed on Jun. 26, 2008, provisional application No. 61/150,530, filed on Feb. 6, 2009.

(51) Int. Cl.
*G01N 33/53* (2006.01)
(52) U.S. Cl. ...... 435/7.1; 424/140.1; 424/811; 435/413; 435/853
(58) Field of Classification Search .................. None
See application file for complete search history.

(56) References Cited

U.S. PATENT DOCUMENTS

| | | | | |
|---|---|---|---|---|
| 3,992,520 | A * | 11/1976 | Gwatkin | 424/172.1 |
| 5,851,817 | A * | 12/1998 | Hardy et al. | 435/252.3 |
| 6,383,496 | B1 | 5/2002 | Curtiss, III et al. | |
| 6,923,958 | B2 | 8/2005 | Xiang et al. | |
| 7,094,868 | B2 | 8/2006 | Samoylova et al. | |
| 2009/0280137 | A1 * | 11/2009 | Samoylova et al. | 424/184.1 |

OTHER PUBLICATIONS

Zhou et al., Proc. Natl. Acad. Sci. USA, 2002, 99:5241-5246.*
Ke et al. J Biol Chem. Jun. 27, 1997;272(26):16603-9.*
PCT Search Report, PCT/US2008/082800, European Patent Office, Apr. 2, 2009.
Baker et al., "Immunization of Cats and Dogs with an Anti-GnRH Protein Vaccine with Molecular Adjuvantation", Proceedings of the Symposium on Nonsurgical Methods for Pet Population Control, Breckemidge, Colorado, Jun. 24-27, 2004.
Dunbar et al., Isolation, Physiochemical Properties and Macromolecular Composition of Zona pellucida from Porcine Oocytes:, Biochemistry 19, 1980: 356-365.
Engmann et al., "Outcome of in vitro fertilization treatments in patients who electively inseminate a limited number of oocytes to avoid creating surplus human embryos for cryopreservation", Fertility and Sterility, Nov. 2005, 84 (5):1406-1410.
Fang et al., "The potential of phage display virions expressing malignant tumor specific antigen MAGE-AI epitope in murine model", Vaccine, 23, 4860-4866, 2005.
Fayrer-Hosken et al., "Immunocontraception of African elephants" Nature 407: 149-150, 2000.
Gaubin et al., "Processing of Filamentous Bacteriophage Virions in Antigen-Presenting Cells Targets Both HLA Class I and Class II Peptide Loading Compartments" DNA Cell Bioloby, vol. 22(1):11-8, Nov. 1, 2003.
Hay et al., "Canine Spermatozoa Cryopreservation and Evaluation of Gamete Interaction", Theriogenology 48: 1329-1342, 1997.
Ivanova et al., "Effect of Cryopreservation of Zona-Binding Capacity of Canine Spermatozoa In Vitro", Theriogenology 1999;52:163-170.
Kehoe et al., "Filamentous Phage Display in the New Millenium", Chem. Rev. 2005, 105, 4056-4072.
Lea et al., "A Chimeric Sperm Peptide Induces Antibodies and Strain-Specific Reversible Infertility in Mice," Biology of Reproduction, vol. 59, pp. 527-536, (1998).
Mastromonaco et al., "The effects of oocyte storage and cumulus cell presence on canine Zona penetration by domestic dog spermatozoa", Theriogenology 57: 1123-1134, 2002.
Millar et al., "Vaccination with a Synthetic Zona pellucida Peptide Produces Long-Term Contraception in Female Mice", Science 1989; 246: 935-938.
Naz et al., "Human Sperm-Specific Peptide Vaccine That Causes Long-Term Reversible Contraception", Biology of Reproduction, 2002, 67:674-680.
Naz, "Human Synthetic Peptide Vaccine for Contraception Targeting Sperm", Archives of Andrology, 2004; 50:113-119.
O'Rand et al., "Inhibition of Fertility in Female Mice by Immunization with B-cell Epitope, the Synthetic Sperm Peptide, P10G," Journal of Reproductive Immunology, vol. 25, pp. 89-102, (1993).
Paterson et al., "Immunocontraception with Zona pellucida Proteins", Cells Tissues Organs 2000, 166:228-232.
Samoylova, Smith, "Identification of Cell Targeting Ligands Using Random Peptide-Presenting Phage Libraries". In Genetic Library Construction and Screening. Advanced Techniques and Applications. C. Bird and B. Smith, eds., Springer-Verlag, Heidelberg, pp. 209 231, 2002.
Samoylova et al., "Targeting peptides for microglia identified via phage display", Journal of Neuroimmunology, 127:13-21, 2002.
Smith "Filamentous Fusion Phage: Novel Expression Vectors that Display Cloned Antigens on the Virion Surface", Science 1985,228: 1315-1317.
Wernette et al., "CpG oligodeoxynucleotides stimulate canine and feline immune cell proliferation", Veterinary Immunology and Immunopathology 2002; 84 : 223-236.
Wheir et al., "Immuno-Sterilization in Dogs Using Zona Pellucida (ZP)Based Vaccine", Proceedings of the Symposium on Nonsurgical Methods for Pet Population Control, Breckenridge, Colorado, Jun. 24-27, 2004.
Yip et al., "Comparison of phage pIII, pVIII and GST as carrier proteins for peptide immunisation in Balb/c mice", Immunology Letters 79(3):197-202, 2001.

(Continued)

*Primary Examiner* — Michael Szperka
(74) *Attorney, Agent, or Firm* — Andrus, Sceales, Starke & Sawall, LLP

(57) ABSTRACT

Disclosed are methods of identifying peptides and compositions that bind to oocytes of animals in a species-specific manner. The methods utilize phage libraries and oocytes isolated from target species and non-target species.

9 Claims, 6 Drawing Sheets

OTHER PUBLICATIONS

Conner et al., "Cracking the egg: increased complexity in the Zona pellucida", Human Reproduction, Jan. 2005, 169(1):17-27.

Ditchkoff et al., "Ecology and management of feral hogs", Human-Wildlife Conflicts, 2007, 1(2):149-151.

Hammond et al., "Porcine adenovirus as a delivery system for swine vaccines and immunotherapeutics", Vet J, Jan. 2005, 169(1):17-27.

Hutton et al., "Disease risks associated with increasing feral swine numbers and distribution in the United States", Midwest Association of Fish and Wildlife Agencies, 2006.

Killian et al., "Immunocontraception of Florida feral swine with a single-dose GnRH vaccine", American Journal of Reproductive Immunology, 2006, 55:378-384.

Miller et al., "Immunocontraception of white-tailed deer with GnRH vaccine", American Journal of Reproductive Immunology, 2000, 44(5):266-274.

Chamley et al., "Antisperm antibodies and conception", Semin Immunopathology, 2007, 29:169-184.

Cowled et al., "Vacination of feral pigs (*Sus scrofa*) using iophenoxic acid as a simulated vaccine", Australian Veterinary Journal, Jan.-Feb. 2008, 86(1 & 2):50-55.

Naz et al., "Identification of Human Sperm Peptide Sequence Involved in Egg Binding for Immunocontraception", Biology of Reproduction, 2000, 62:318-324.

Naz et al., "Recent advances in contraceptive vaccine development", Human Reproduction, Aug. 19, 2005, 1-13.

Shata et al., "Recent advances with recombinant bacterial vaccine vectors", Molecular Medicine Today, Feb. 2000, 6:66-71.

Suri, "Contraceptive vaccines targeting sperm", Expert Opin. Biol. Ther., 2005, 5(3):381-392.

Suri, "Sperm-based contraceptive vaccines: current status, merits and development", Expert Reviews in Molecular Medicine, Sep. 12, 2005, 7(18).

Szardenings et al., "Phage Display Selection on Whole Cells Yields a Peptide Specific for Melanocortin Receptor 1", Journal of Biological Chemistry, Oct. 31, 1997, 272(44):27943-27948.

"Lab FAQs: Find a Quick Solution", 3rd Edition, published by Roche Applied Science, https://www.roche-applied-science.com/PROD_INF/MANUALS/labfaqs/lab_faqs.pdf, available Mar. 22, 2011.

Engmann et al., "Outcome of in vitro fertilization treatment in patients who electively inseminate a limited number of oocytes to avoid creating surplus human embryos for cryopreservation", Fertility and Sterility, Nov. 2005; 84 (5):1406-10.

Brown et al., "A single administration immunocontraceptive vaccine for grey seals", Nature, 1996, 379:30-31.

Daudel et al., "Use of attenuated bacteria as delivery vectors for DNA vaccines", Expert Review of Vaccines, 2007, 6 (1):97-110.

Garmory et al., "The Use of Live Attenuated Bacteria as a Delivery System for Heterologous Antigens", Journal of Drug Targeting, 2003, 11(8-10):471-479.

Gentschev et al., "Recombinant attenuated bacteria for the delivery of subunit vaccines", Vaccine, 2001, 19:2621-2628.

Harris, "Swine ZP and Dog Immunocontraception", Proceedings of the Symposium on Nonsurgical Methods for Pet Population Control, Jun. 24-27, 2004.

Jewgenow et al., "Antigenic and Antifertile Determinants of Feline Zona Pellucida B Protein—A Strategy for Contraceptive Vaccine Development", Proceedings of the Symposium on Nonsurgical Methods for Pet Population Control, Jun. 24-27, 2004.

\* cited by examiner

FIG. 5

Sequences
SEQ ID NO:1  - daddqthrrfsm
SEQ ID NO:2  - danrlphpanin
SEQ ID NO:3  - dlnghktlpvsk
SEQ ID NO:4  - niglphdlhkrl
SEQ ID NO:5  - glhnnlhattpe
SEQ ID NO:6  - qsaawypwsadh
SEQ ID NO:7  - ytvsmpnvkdaa
SEQ ID NO:8  - ympnpftaskwk
SEQ ID NO:9  - gqimplptnllv
SEQ ID NO:10 - sttlpmgsnahl
SEQ ID NO:11 - tylkadslfsrv

Motifs
SEQ ID NO:12 - ttlxtxsxxhxx
SEQ ID NO:13 - dxnxlphxxxxx
SEQ ID NO:14 - xglxxxlhxtxp
SEQ ID NO:15 - xxmpn{p,v}xxax
SEQ ID NO:16 - x{g,s}xxtlpxsx
SEQ ID NO:17 - qxaxxxpwxxxx

FIG. 6

Sequences
SEQ ID NO:2  - danrlphpanin
SEQ ID NO:18 - tlgwtaneaprr
SEQ ID NO:19 - lladtthhrpwt
SEQ ID NO:20 - sqspamysqtrp
SEQ ID NO:21 - avtqhlkfkgfn
SEQ ID NO:22 - anfnmthhqghk

Motifs
SEQ ID NO:23 - xxtthhxxxxxx
SEQ ID NO:24 - xxnxxlxxpaxx
SEQ ID NO:25 - xxaxxxxxrpxx
SEQ ID NO:26 - xxssxxsasxxx

US 8,158,366 B2

METHODS OF IDENTIFYING PEPTIDES AND COMPOSITIONS THAT BIND TO OOCYTES IN A SPECIES-SPECIFIC MANNER

CROSS-REFERENCE TO RELATED APPLICATIONS

The present application claims the benefit of priority under 35 U.S.C. §119(e) to U.S. provisional application No. 61/123,275, filed on Apr. 7, 2008; U.S. provisional application No. 61/130,473, filed on May 30, 2008; U.S. provisional application No. 61/133,201, filed on Jun. 26, 2008; and U.S. provisional application No. 61/150,530, filed on Feb. 6, 2009, the contents of which are incorporated herein by reference in their entireties.

BACKGROUND

The present subject matter relates to the fields of peptide and polypeptide selection, immunology, and targeted contraception in animals. In particular, the present subject matter relates to peptides and polypeptides that bind to the zona pellucida (ZP) of oocytes, methods for selecting such peptides and polypeptides, vectors that express the selected peptides and polypeptides, and compositions that comprise such peptides, polypeptides, or vectors (e.g., compositions for inducing an immune response against sperm).

Overpopulation of animals of multiple species including domestic, feral, and wild animals results in various economic, health, and security problems. For example, feral swine cause significant physical damage to agricultural crops, soils, vineyards, tree plantings, turf, rare plant communities, wildlife habitat, archaeological sites, and vehicles. (See Ditchkoff S S, West B C. Ecology and management of feral hogs. Human-Wildlife Conflicts 2007; 1(2):149-151). Feral swine compete with livestock and native wildlife for food, and prey on domestic animals and wildlife. Feral swine carry at least thirty important viral and bacterial diseases and thirty-seven parasites that affect humans, pets, livestock, and wildlife (e.g., brucellosis, salmonellosis, diseases due to pathogenic *E. coli* strains, rabies, tuberculosis, and tularemia). Feral swine also could potentially spread additional human and animal diseases not currently found in the United States. (See Hutton T, DeLiberto T, Owen S, Morrison B. Disease risks associated with increasing feral swine numbers and distribution in the United States. Midwest Association of Fish and Wildlilfe Agencies 2006). Control programs for feral swine eradication such as poisoning, trapping, shooting, etc., are ineffective, expensive and generally unacceptable to the public. Currently available contraceptives for animals are not selective and affect multiple species and, therefore, cannot be permitted for use in uncontrolled environments such as natural habitats of feral or wild animals. (See Miller L A, Johns B E, Killian G J. Immunocontraception of white-tailed deer with GnRH vaccine. Am J Reprod Immunol 2000; 44(5):266-274; and Killian G, Miller L, Rhyan J, Doten H. Immunocontraception of Florida feral swine with a single-dose GnRH vaccine. American Journal of Reproductive Immunology 2006; 55:378-384). Thus, there is an urgent need for immunocontraceptive, species-specific vaccines that can affect the target species only and be delivered via economically sound oral or oronasal administration. Additional examples of species, the overpopulation of which imposes various kinds of economic and health risks, include coyotes, deer, and raccoons.

SUMMARY

Disclosed are methods, compositions, zona pellucida (ZP)-binding peptides, and vectors for expressing the peptides for use in immunocontraception of animals. The disclosed compositions may include immunogenic or vaccine compositions that comprise ZP-binding peptides or vectors that express the ZP-binding peptides. The disclosed compositions also may include bait compositions that comprise the immunogenic or vaccine compositions.

Preferably, the ZP-binding peptides, the vectors, the immunogenic or vaccine compositions, and the bait compositions are species-specific. For example, preferably the peptides and polypeptides bind specifically to the ZP of oocytes of a target species of animal and do not bind to the ZP of oocytes of a non-target species of animal. The peptides and polypeptides may be expressed via vectors that include viral, bacterial, or other vectors. Preferably, the vector is species-specific in that the vector infects or expresses the peptide or polypeptide in a selected species of animal and does not infect or express the peptide or polypeptide in a non-selected species of animal. The compositions disclosed herein may comprise the peptides, polypeptides, or vectors that express the peptides or polypeptides. The disclosed compositions may be immunogenic or vaccinogenic and may be administered to animals for species-specific immunocontraception via induction of a species-specific anti-sperm immune response. The compositions may be formulated as bait compositions that also are species-specific in that they attract a selected species of animal and do not attract a non-selected species of animal.

The disclosed methods include methods for identifying a peptide or polypeptide that binds specifically to the zona pellucida of oocytes from a target species of animal. The methods may include: (a) isolating oocytes from one or more mammals (e.g., porcine oocytes, feline oocytes, canine oocytes, or bovine oocytes); (b) contacting the oocytes with a phage library; (c) selecting phage that bind specifically to the oocytes of a target species of animal (e.g. phage that bind specifically to porcine oocytes as compared to oocytes from other animals (e.g., feline oocytes, canine oocytes, or bovine oocytes)), thereby identifying peptides that bind to the ZP of the oocytes of the target animal species. The methods may include: (a) contacting oocytes of one or more species of animal with a phage library; (b) separating phage that do not bind to the oocytes of one or more non-target species of animal (e.g., feline oocytes, canine oocytes, and bovine oocytes) from the phage library; and (c) contacting the separated phage with oocytes of a target species of animal (e.g., porcine oocytes); and (d) separating phage that bind to the oocytes of the target species of animal (e.g., porcine oocytes), thereby identifying peptides that selectively bind to the ZP of the oocytes of the target animal species (e.g., porcine oocytes). Alternatively, the methods may include: (a) contacting oocytes of one or more species of animal with a phage library; (b) separating phage that bind to the oocytes of the target species of animal (e.g., porcine oocytes) from the phage library; and (c) contacting the separated phage with oocytes of one or more non-target species of animal (e.g., feline oocytes, canine oocytes, or bovine oocytes); and (d) separating phage that do not bind to the oocytes of the one or more non-target species of animal, thereby identifying peptides that selectively bind to the ZP of the oocytes of the target animal species (e.g., porcine oocytes). In the disclosed methods, the phage library may be contacted with a relatively small number of oocytes (e.g., less than about 1000 oocytes).

Also disclosed are peptide or polypeptide identified by the disclosed methods. In some embodiments, the identified peptides or polypeptides may include an amino acid sequence selected from a group consisting of SEQ ID NO:2 (DANRLPHPANIN), SEQ ID NO:18 (TLGWTANEAPRR), SEQ ID NO:19 (LLADTTHHRPWT), SEQ ID NO:20 (SQSPAM- YSQTRP), SEQ ID NO:21 (AVTQHLKFKGFN), and SEQ ID NO:22 (ANFNMTHHQGHK). Also disclosed are polynucleotides encoding the identified peptides or polypeptides. The polynucleotide may be operably linked to a promoter sequence as a recombinant polynucleotide. The recombinant polynucleotide may be present in a vector which is utilized to transform an isolated cell. Preferably, the vector is capable of expressing the encoded peptide or polypeptide. The encoded peptide or polypeptide may be produced by a method that includes: a) culturing the transformed cell under conditions suitable for expression of the polypeptide; and b) recovering the polypeptide so expressed. Alternatively, the peptide may be prepared by a synthetic method.

The identified peptides or polypeptides may be utilized as antigens. In some embodiments, the identified peptides or polypeptides may be modified to enhance antigenicity. For example, the peptides or polypeptides may be conjugated to one or more carrier proteins (e.g., keyhole-limpet hemocyanin (KLH)).

The disclosed compositions may include immunogenic compositions or vaccine compositions. In some embodiments, the compositions include (a) one or more polypeptides comprising an amino acid sequence selected from a group consisting of SEQ ID NO:2 (DANRLPHPANIN), SEQ ID NO:18 (TLGWTANEAPRR), SEQ ID NO:19 (LLADTTH-HRPWT), SEQ ID NO:20 (SQSPAMYSQTRP), SEQ ID NO:21 (AVTQHLKFKGFN), and SEQ ID NO:22 (ANFN-MTHHQGHK); and (b) a suitable excipient, carrier, or diluent. For example, the compositions may include two or more polypeptides, where each of the two or more polypeptides comprise an amino acid sequence selected from a group consisting of SEQ ID NO:2 (DANRLPHPANIN), SEQ ID NO:18 (TLGWTANEAPRR), SEQ ID NO:19 (LLADTTH-HRPWT), SEQ ID NO:20 (SQSPAMYSQTRP), SEQ ID NO:21 (AVTQHLKFKGFN), and SEQ ID NO:22 (ANFN-MTHHQGHK). The immunogenic compositions or vaccine compositions may further include an adjuvant as disclosed herein. The immunogenic compositions or vaccine compositions further may include an immunostimulatory agent (e.g., an immunostimulatory oligodeoxynucleotide such as CpG).

Also disclosed are vectors that express the disclosed peptides or polypeptides. Suitable vectors include, but are not limited to, viral vectors and bacterial vectors. The vector may be species-specific (e.g., a viral vector that specifically infects a swine). The vectors may be formulated as an immunogenic composition or a vaccine composition. In some embodiments, the immunogenic compositions or vaccine compositions comprise one or more vectors (e.g., species-specific vectors) that express one or more species-specific peptides or polypeptides (e.g. species-specific ZP-binding peptides or polypeptides).

The disclosed compositions also may include bait compositions for attracting a target species of animal. For example, the disclosed composition may include species-specific bait compositions for swine (e.g., feral swine). The bait compositions may include ZP-binding peptides (e.g., as disclosed herein), vectors that express the ZP-binding peptides, immunogenic compositions that include ZP-binding peptides, or vaccine compositions that include the ZP-binding peptides. The bait compositions thereof may be specific-specific in one or more aspects, including but not limited to: (1) the bait compositions attract a target species of animal (e.g., a swine); (2) the bait compositions comprise a species-specific vector (e.g., a viral vector that infects specifically a target species of animal or that is capable of replicating or expressing an encoding protein only in a target species of animal); (3) the bait composition comprises species-specific ZP-binding peptides or polypeptides or comprises vectors that express species-specific ZP-binding peptides or polypeptides.

Also disclosed are methods for using the peptides, polypeptides, or compositions that contain the peptides or polypeptides. The disclosed methods may include administering the disclosed immunogenic compositions or vaccine compositions (optionally formulated as a bait composition) to an animal in order to induce an immune response (e.g., an anti-sperm antibody response, a T-cell response, or both). The disclosed methods may include methods for producing antibodies that bind to sperm (e.g., anti-swine sperm antibodies). As such, the compositions may include an effective amount of a peptide or polypeptide (e.g., a ZP-binding peptide) for inducing an immune response against sperm. Alternatively, the compositions may include a vector that expresses an effective amount of a peptide or polypeptide (e.g., a ZP-binding peptide) for inducing an immune response against sperm. In the methods, the compositions may be administered to an animal of either sex (i.e., male or female). The methods further may include isolating the induced antibodies from a sample obtained from the animal (e.g., from blood or a blood product such as serum or plasma).

The disclosed methods also may include methods for immunizing an animal against conception (i.e., immunocontraceptive methods). The methods may include administering the disclosed immunogenic composition or vaccine compositions (optionally formulated as bait compositions) to an animal such as a female swine, thereby immunizing the animal against conception. In some embodiments, the animal is immunized for a temporary period of time (e.g., for a period of weeks or months).

BRIEF DESCRIPTION OF THE FIGURES

FIG. 5. provides a list of porcine ZP-binding peptide sequences and motifs identified in Experiment 1 by selection from a PhD-12 phage display library on intact porcine oocytes surrounded by ZP as described in Example 1.

FIG. 6. provides a list of porcine-specific ZP-binding peptide sequences and motifs identified in Experiment 2 by selection from a PhD-12 phage display library on intact porcine oocytes surrounded by ZP subsequent to subtractive selection on non-porcine oocytes (i.e., feline oocytes, canine oocytes, and bovine oocytes).

DETAILED DESCRIPTION

Figure 1:
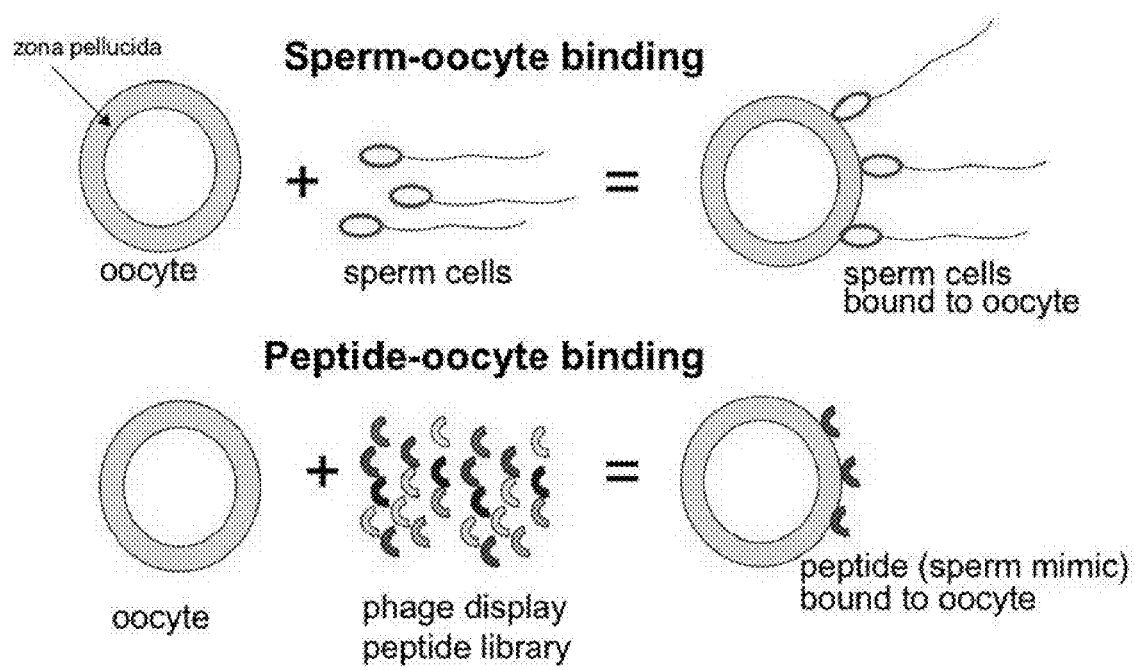
FIG. 1. illustrates a method whereby phage display peptide libraries are used to identify peptides mimicking sperm surface peptides or proteins that bind to zona pellucida at fertilization.

The disclosed subject matter is further described below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≦10% of the particular term and "substantially" and "significantly" will mean plus or minus >10% of the particular term.

As used herein, the terms "include" and "including" have the same meaning as the terms "comprise" and "comprising."

The terms "subject" and "patient" may be used interchangeably herein. A patient or subject may refer to a non-human patient or subject at risk for conception (e.g., a swine including a feral swine). The term "swine" as used herein is meant to include domesticated, wild, and feral swine (e.g., *Sus scrofa*) and may be used interchangeably with the term "pig" or "porcine."

The term "sample" is used in its broadest sense. A sample may comprise a bodily fluid (e.g., blood or a blood product such as serum or plasma obtained from a subject or patient).

The disclosed methods may include contacting isolated oocytes with a phage library. As utilized herein, the term "contacting" may include placing the isolated oocytes and the phage library in a reaction vessel and reacting or incubating the isolated oocytes and phage library under conditions that promote interaction between the isolated oocytes and the phage library. The disclosed methods may include separating phage that bind to the oocytes (or that do not bind to the oocytes) from the phage library. As utilized herein, the term "separating" may be utilized interchangeably with the term "isolating" or "removing."

One aspect of the present disclosure relates to methods for isolating peptides and polypeptides that bind to the ZP of oocytes via phage display. Methods for performing phage display are known in the art. (See, e.g., U.S. Pat. No. 7,094,868, which discloses isolating peptides by phage display, the content of which is incorporated herein by reference in its entirety). Related methods for phage display and isolation of ZP-binding peptides are disclosed in U.S. patent application Ser. No. 12/266,944, filed on Nov. 7, 2008, the content of which is incorporated herein by reference in its entirety.

In particular, the methods disclosed herein may be utilized to isolate peptides and polypeptides that bind selectively to ZP of oocytes of a target species of animal relative to ZP of oocytes of a non-target species of animal via phage display. The methods may include: (a) isolating oocytes from one or more species of animal (e.g., porcine oocytes, feline oocytes, canine oocytes, or bovine oocytes); (b) contacting the oocytes with a phage library; (c) selecting phage that bind to the oocytes (e.g., phage that bind selectively to oocytes of one species of animal), thereby identifying peptides that bind to the ZP of the oocytes. Surprisingly, in the disclosed methods, the phage library may be contacted with a relatively small number of oocytes (e.g., less than about 1000 oocytes). It is generally understood in the field of phage display technology that a significant number of cells (typically millions) are needed for successful selection of cell-binding peptides on intact cells. This significant number of cells is easily achievable for the vast majority of cell types via propagation in cell culture media. However, oocytes cannot be obtained through cell culturing and oocytes with surrounding ZP should be isolated directly from ovaries removed from animals. Generally, only a small number of oocytes can be isolated from a single pair of mammalian ovaries (i.e., as a few as 2-3 and on average, several dozen), depending on the animal species and its age and condition). As such, it would be expected that many animals would be required in order to obtain a sufficient number (millions) of oocytes for phage display selection protocols commonly in use. In addition to the huge numbers of animals needed for isolating a sufficient number of oocytes, the oocyte isolation procedure is very time consuming and generally takes several hours for an experience technician to isolate even a relatively small number of oocytes. Thus, it would take thousands of animals and years of work to isolate the number of oocytes required by currently accepted protocols. For these reasons, millions of oocytes cannot be readily available for the use in phage display selection protocols that are generally utilized in the field. Therefore, herein, a phage display selection procedure that requires no more than 1000 oocytes surrounded by ZP was developed.

The peptides and polypeptides contemplated herein bind specifically to ZP. Furthermore, the peptides and polypeptides contemplated herein may be utilized in immunogenic compositions or vaccines for eliciting antibodies that bind specifically to sperm. In this regard, the terms "binds specifically" and "bind specifically" refer to that interaction between the polypeptide (or peptide) and the ZP; or to that interaction between sperm and an antibody (or other binding molecule). The interaction is dependent upon the presence of a particular structure of the protein, e.g., the antigenic determinant or epitope present on the polypeptide or peptide, recognized by the antibody or binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The peptides and polypeptides disclosed herein may be described via their "amino acid sequence." As used herein, the term "amino acid sequence" refers to an oligopeptide, peptide, polypeptide, or protein sequence, or a fragment of any of these, and to naturally occurring or synthetic molecules. The terms "peptide" and "polypeptide" may be used interchangeably herein. Generally, the term "peptide" refers to an amino acid polymer having a relatively low number of amino acid residues (e.g., no more than about 50, 40, 30, 20, 15, 12, or 7 amino acid residues). For the most part, peptides will comprise at least about 7 to about 50 amino acids, preferably at least about 7 to about 30 amino acids, more preferably about 7 to about 8, 9, 10, 11, 12, 13, 14, 15, 16, 17, 18, 19, or 20 amino acids. Generally, the term "polypeptide" refers to an amino acid polymer having a greater number of amino acid residues than a peptide. The term "protein" also may be used herein interchangeably with the term "polypeptide."

The presently disclosed peptides may be synthetic. As used herein, "synthetic peptide" refers to a peptide which has an amino acid sequence which is not a native sequence or is not in its native context and which confers on phage displaying it the ability to bind or preferentially bind to a particular cell population. By "not in its native context" is intended that the peptide is substantially or essentially free of amino acid sequences that naturally flank the amino acid sequence of the peptide in the native protein which comprises the amino acid sequence of the peptide. For example, a synthetic peptide which is not in its native context may be flanked at either or both ends by no more than 50, 40, 30, 20, 10, 9, 8, 7, 6, 5, 4, 3, 2, or 1 amino acid(s) found in the native protein.

The peptides and polypeptides disclosed herein may exhibit at least two-fold, three-fold, four-fold, five-fold, six-fold, seven-fold, ten-fold, twenty-fold, thirty-fold or more increased binding affinity for ZP of oocytes relative to at least one category or type of other cell. Peptides and polypeptide that exhibit such binding characteristics are said to exhibit preferential binding to ZP. Peptides and polypeptides that do not exhibit at least a two-fold increased binding affinity for ZP relative to another category or type of other cell but that bind to ZP are simply said to bind to ZP.

Preferably, the peptides and polypeptides disclosed herein selectively bind to ZP of oocytes of a target species (e.g., ZP of porcine oocytes) relative to ZP of oocytes of a non-target species (e.g. feline oocytes, canine oocytes, or bovine oocytes). In this regard, the peptides and polypeptides may be referred to as "species-specific." In some embodiments, the species-specific peptides and polypeptides disclosed herein may exhibit at least two-fold, three-fold, four-fold, five-fold, six-fold, seven-fold, ten-fold, twenty-fold, thirty-fold or more increased binding affinity for ZP of oocytes of a target species relative to ZP of oocytes of a non-target species.

As used herein, the term "nucleic acid sequence" refers to a nucleotide, oligonucleotide, polynucleotide, or any fragment thereof. As used herein, the term "polynucleotide" refers to a nucleotide polymer. A polynucleotide may encode a peptide or polypeptide as disclosed herein. A polynucleotide may be operably linked to a heterologous promoter sequence as a recombinant polynucleotide. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. A recombinant polynucleotide comprising a polynucleotide operably linked to a promoter sequence may be present in a vector (e.g., a plasmid) which may be utilized to transform a host cell (e.g., where the vector further includes a selectable marker).

The presently disclosed peptides and polypeptide may be isolated or substantially purified. The terms "isolated" or "substantially purified" refers to peptides or polypeptides that are removed from their natural environment and are isolated or separated, and are at least 60% free, preferably at least 75% free, and most preferably at least 90% free from other components with which they are naturally associated.

Also disclosed are peptide and polypeptides identified by the phage display method, and preferably include species-specific ZP-binding peptide and polypeptides. Peptides identified herein include peptides having the amino acid sequence or motifs of SEQ ID NOs:1-26 (preferably SEQ ID NOs:2 or 18-26). Also disclosed are polypeptides comprising the amino acid sequence or motifs of any of SEQ ID NOs:1-26, polynucleotides encodings such polypeptides, recombinant polynucleotides comprising such polynucleotides, expression vectors, and methods for expressing the encoded polypeptide.

The peptides disclosed herein may be fused or conjugated to one or more other peptides or non-peptide moieties (e.g., in order to provide an antigen). For example, a fusion polypeptide as contemplated herein may include a fusion of any of the peptides or motifs of SEQ ID NO:1-26 and one or more other immunogenic peptides. The peptides disclosed herein may be present in a polypeptide (e.g., where the polypeptide comprises one or more copies of the amino acid sequence of the peptide, optionally in tandem). The disclosed peptides may be modified to enhance immunogenicity. For example, the peptides disclosed herein may be conjugated to one or more carrier proteins (e.g., keyhole-limpet hemocyanin).

The disclosed methods may include inducing an immune response against one or more peptides that bind to the ZP (e.g., an immune response against one or more species-specific peptides that bind to the ZP). In some embodiments, the methods include inducing polyclonal antibodies against one or more peptides that bind to the ZP by administering to an animal an immunogenic composition that includes one or more of the peptides (and preferably, one or more specific peptides) or that includes one or more vectors that express one or more of the peptides. The animal may be a non-human animal (e.g., a swine). The induced polyclonal antibodies may include anti-sperm antibodies. The methods disclosed herein also may include preventing conception by administering to the animal an immunogenic composition that includes one or more peptides that bind to the ZP (and preferably, one or more specific peptides that bind to the ZP) or that includes one or more vectors that express one or more of the peptides. For example, an animal (e.g., a non-human animal such as a swine) may be protected against conception by administering to the animal a composition that includes one or more peptides that bind to the ZP or that includes one or more vectors that express one or more peptides that bind to the ZP.

The disclosed compositions may be administered as immunogenic compositions or vaccines utilizing a selected "prime-boost vaccination regimen." As used herein, a "prime-boost vaccination regimen" refers to a regimen in which a subject is administered a first composition one or more times (e.g., one time or two or three times with about 2, 3, or 4 weeks between administrations) and then after a determined period of time after having administered the first composition (e.g., about 2 weeks, about 4 weeks, about 2 months, about 3 months, about 4 months, about 5 months, about 6 months, or longer), the subject is administered a second composition. The second composition may also be administered more than once, with at least 2, 3, or 4 weeks between administrations. The first and second compositions may be the same or different.

Also disclosed are immunogenic compositions and vaccines for performing the disclosed methods. An immunogenic composition may be monovalent or polyvalent. Typically, the immunogenic compositions include one or more peptides that bind to the ZP (e.g., species-specific ZP-binding peptides), or the immunogenic compositions include one or more vectors that express one or more peptides that bind to the ZP (e.g., species-specific vectors that express species-specific ZP-binding peptides). The immunogenic compositions also may include a suitable excipient, carrier, or diluent.

Suitable peptides for the immunogenic compositions (or for expression by vectors of the immunogenic compositions) may include one or more polypeptides comprising the amino acid sequence of a peptide as disclosed herein, for example one or more polypeptides comprising the amino acid sequence or motifs of any of SEQ ID NOs:1-26. In some embodiments, the immunogenic compositions may include two or more polypeptides (or two or more vectors that express two or more polypeptides) where each polypeptide of the two or more polypeptides comprises the amino acid sequence or motifs of any of SEQ ID NOs:1-26. The immunogenic compositions may include an isolated polypeptide or peptide at a concentration sufficient to induce an immunogenic response against sperm (e.g., via antibody induction, a T-cell response, or both), or the immunogenic compositions may include one or more vectors that express the polypeptide or peptide at a concentration sufficient to induce an immunogenic response against sperm (e.g., via antibody induction, a T-cell response, or both). In some embodiments, the immunogenic compositions may include at least about 10 µg of the isolated polypeptide or peptide (or preferably, at least about 100 µg of the isolated polypeptide or peptide).

The "immunogenic compositions" and "vaccines" disclosed herein are capable of stimulating an immune response in an animal inoculated with the immunogenic composition or vaccine. An immune response may include induction of antibodies, induction of a T-cell response, or both. Herein, the term "prevention" when used in reference to an immunogenic composition or vaccine may refer to the partial or complete prevention against conception via an immune response induced by the immunogenic composition or vaccine.

An "an immunogenic composition comprising a given peptide or polypeptide" refers to a composition containing the given peptide or polypeptide. The composition may comprise a dry formulation or an aqueous solution. An "immunogenic peptide or polypeptide" is an antigen which is capable of eliciting an immune response when introduced into an animal, for example, a swine.

The methods disclosed herein may include administering an immunogenic composition or a vaccine to an animal. An "animal," as used herein, may include a non-human animal (e.g., a swine).

The methods disclosed herein also may include protecting an animal against conception or preventing an animal from conceiving by administering to the animal a composition (e.g., a bait composition) that includes an isolated peptide as disclosed herein or that includes a vector that expresses the peptide. The administered composition may include an immunogenic composition or a vaccine composition. For example, an animal (e.g., a swine) may be protected against conception by administering to the animal a bait composition that includes an isolated polypeptide comprising an amino acid sequence or motif of any of SEQ ID NOs:1-26 or a vector that expresses a polypeptide comprising an amino acid sequence or motif of any of SEQ ID NOs:1-26. The compositions disclosed herein may further include a suitable excipient, carrier, or diluent.

The presently disclosed peptide or polypeptide may be expressed by viral vectors or bacterial vectors (e.g., as included a part of an immunogenic composition, vaccine, or bait composition). As used herein, a "viral vector" (e.g., an adenovirus, Sendai virus, or measles virus vector) refers to recombinant viral nucleic acid that has been engineered to express a heterologous polypeptide. The recombinant viral nucleic acid typically includes cis-acting elements for expression of the heterologous polypeptide. The recombinant viral nucleic acid typically is capable of being packaged into a helper virus that is capable of infecting a host cell. For example, the recombinant viral nucleic acid may include cis-acting elements for packaging. Typically, the viral vector is not replication competent or is attenuated. An "attenuated recombinant virus" refers to a virus that has been genetically altered by modern molecular biological methods (e.g., restriction endonuclease and ligase treatment, and rendered less virulent than wild type), typically by deletion of specific genes. For example, the recombinant viral nucleic acid may lack a gene essential for the efficient production or essential for the production of infectious virus. Recombinant attenuated bacteria also may be utilized as vectors in the pharmaceutical compositions and vaccines disclosed herein (e.g., recombinant attenuated Shigella, Salmonella, Listeria, or Yersinia). Recombinant bacterial vaccine vectors are described in Daudel el al., "Use of attenuated bacteria as delivery vectors for DNA vaccines," Expert Review of Vaccines, Volume 6, Number 1, February 2007, pp. 97-110(14); Shata et al., "Recent advances with recombinant bacterial vaccine vectors," Molec. Med. Today (2000), Volume 6, Issue 2, 1 Feb. 2000, pages 66-71; Clare & Dougan, "Live Recombinant Bacterial Vaccines," Novel Vaccination Strategies, Apr. 16, 2004 (Editor Stefan H. E. Kaufman); Gentschev et al., "Recombinant Attenuated Bacteria for the Delivery of Subunit Vaccines," Vaccine, Volume 19, Issues 17-19, 21 Mar. 2001, Pages 2621-2628; Garmory et al., "The use of live attenuated bacteria as a delivery system for heterologous antigens," J. Drug Target. 2003; 11(8-10):471-9; U.S. Pat. Nos. 6,383,496; and 6,923,958 (which all are incorporated by reference herein in their entireties). Preferably, the vector is species-specific, whereby the vector selectively infects a target species of animal or the vector selectively expresses an encoded heterologous peptide in the target species of animal after infecting the animal. Suitable viral vectors for expressing the peptides and polypeptides disclosed herein include porcine adenovirus.

The immunogenic compositions or vaccines may be formulated for delivery in any suitable manner. For example, the immunogenic compositions or vaccines may be formulated for at least one of oral delivery, intranasal delivery, intramuscular delivery, subdermal delivery, subcutaneous delivery, intravenous delivery, and intraperitoneal delivery. The immunogenic compositions or vaccines can be administered using a variety of methods including intranasal and/or parenteral (e.g., intramuscular) administration. In some embodiments of the methods, the immunogenic composition or vaccine is administered intramuscularly one or more times at suitable intervals (e.g., at intervals of 2-4 weeks), followed by administration of the immunogenic composition or vaccine at least once intramuscularly or intranasally after a suitable time period (e.g., 2-4 weeks after the last parenteral administration of vaccine). The immunogenic compositions or vaccines may be administered to an animal of either sex. In some embodiments, the animal is female.

The present immunogenic composition and vaccines may be formulated with a pharmaceutically or veterinarily acceptable excipient, carrier, or diluent. The forms suitable for injectable commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

The present immunogenic composition or vaccines may include an adjuvant. The term "adjuvant" refers to a compound or mixture that is present in an immunogenic composition or vaccine and enhances the immune response to an antigen present in the immunogenic composition or vaccine. For example, an adjuvant may enhance the immune response to a polypeptide present in a vaccine as contemplated herein, or to an immunogenic fragment or variant thereof as contemplated herein. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, nonionic block co-polymer adjuvants (e.g., CRL1005), aluminum phosphates (e.g., $AlPO_4$), R-848 (a Th1-like adjuvant), imiquimod, PAM3CYS, poly (I:C), loxoribine, potentially useful human adjuvants such as BCG (bacille Calmette-Guerin) and Corynebacterium parvum, CpG oligodeoxynucleotides (ODN), cholera toxin derived antigens (e.g., CTA1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

It is generally advantageous to formulate the present compositions in dosage unit form for ease of administration and uniformity of dosage. "Dosage unit form" as used herein refers to physically discrete units suited as unitary dosages for the animal subjects to the treated; each unit containing a predetermined quantity of the active material calculated to produce the desired therapeutic effect in association with the required pharmaceutical carrier. The specification for the dosage unit forms are dictated by and depend on among other factors (a) the unique characteristics of the active material and the particular therapeutic effect to be achieved; (b) the limitations inherent in the art of compounding such active material for the treatment of disease; and (c) the manner of intended administration of the dosage unit form. In some embodiments, a dose of the immunogenic composition or vaccine includes at least about 10 micrograms (preferably 100 micrograms) of one or more isolated polypeptides or peptides as disclosed herein.

Sterile injectable solutions may be prepared by incorporating the isolated polypeptide or peptide in the desired amount in an appropriate solvent with various of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient (i.e., lyophilized form of the active ingredient) plus any additional desired ingredient from a previously sterile-filtered solution thereof.

It also may be advantageous to add a stabilizer to the present compositions. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

The disclosed immunogenic composition, vaccine compositions, and the peptide or expression vectors included therein may be formulated as a species-specific bait composition (e.g., as a contraceptive species-specific bait vaccine). Preferably, the bait composition attracts a target species of animal, such as feral swine, and does not attract a non-target species of animal, such as birds. Feral pig bait compositions are known in the art (see, e.g., PIGOUT® brand feral pig bait (Animal Control Technologies, Somerton, Victoria AU)) and have been utilized for oral vaccination of feral pigs (see, e.g., Ballestreros et al., "Evaluation of baits for oral vaccination of European wild boar piglets," Res. Vet. Sci. 2008 Oct. 22 epub; Cowled et al., "Vaccination of feral pigs (*Sus scrofa*) using iophenoxic acid as a simulated vaccine," Aust. Vet. J. 2008 January-February; 86(1-2):50-5; and Kaden et al., "Oral immunisation of wild boar against classical swine fever: evaluation of the first field study in Germany," Vet. Micro., April 2000, 73(2-3):239-252, which contents are incorporated herein by reference in their entireties).

The disclosed compositions, which may include bait compositions, may be administered to a target species of animal. As contemplated herein, "administering" a composition to an animal may include feeding a bait composition to the animal or depositing a bait composition in locations where the animal is likely to come in contact with the bait composition and smell, touch, taste, or eat the bait composition.

Also disclosed herein are isolated antisera, antibodies, or other binding molecules that bind specifically to the peptides disclosed herein. For example, the antisera, antibodies, or other binding molecules, may include an isolated antibody that binds specifically to a polypeptide consisting of an amino acid sequence or motif of any of SEQ ID NOs:1-26. Preferably, the antisera, antibodies, or other binding molecules disclosed herein also bind specifically to sperm (e.g., swine sperm). The isolated antibody or binding molecule may be of any suitable isotype (e.g., IgG, IgM, IgE, IgD, IgA, and mixtures thereof). The antibodies may be polyclonal or monoclonal. The term "antibody or other binding molecule" refers to intact immunoglobulin molecules as well as to fragments thereof, such as Fab, F(ab')$_2$, and Fv fragments, which are capable of binding an epitopic determinant. The antibodies or other binding molecules may be naturally occurring or synthetic (e.g., scFv). Other binding molecules may include antibody fragments (e.g., Fab fragments), coupled antibodies, and coupled antibody fragments. Antibodies or other binding molecules that bind the presently disclosed peptides and polypeptides can be induced or elicited using the intact peptide or a polypeptide comprising the intact peptide as an immunizing antigen. The polypeptide or oligopeptide used to immunize an animal (e.g., a swine or other animal) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide may then be used to immunize the animal. The antibodies or other specific binding molecules may be conjugated to a suitable therapeutic agent (e.g., a toxin) or a label. The antibodies may be modified for use in therapeutic or diagnostic methods.

Also disclosed herein are kits. The kits may include one or more components for performing the methods disclosed herein. For example, the kits may include one or more of the immunogenic compositions or vaccines for immunizing or vaccinating an animal, where the immunogenic compositions or vaccines optionally are formulated as species-specific bait compositions. The disclosed kits may include components for making the immunogenic compositions or vaccines as disclosed herein, or for formulating bait compositions comprising the immunogenic compositions or vaccines. The components of the disclosed kits may be provided in any suitable form (e.g., liquid form or lyophilized form). Kits further may include solvents for resuspending or dissolving a lyophilized protein.

EXAMPLES

The following Examples are illustrative and are not intended to limit the scope of the claimed subject matter.

Summary

Peptides were identified that mimic sperm surface peptides/proteins that bind to zona pellucida (ZP) at fertilization utilizing phage display selection. (See FIG. 1). ZP is a glycoproteinaceous protective barrier which surrounds each mammalian oocyte and is essential for sperm-oocyte interaction and, therefore, conception. Immunization with ZP-binding peptides (mimicking sperm antigens) stimulates production of anti-peptide antibodies which act as anti-sperm antibodies. Anti-sperm antibodies can reduce fertility by decreasing sperm motility, by inhibiting the acrosome reaction, or by interfering with sperm-oocyte binding. (See Chamley L W, Clarke G N. Antisperm antibodies and conception. Semin Immunopathol 2007; 29(2):169-184; Suri A. Contraceptive vaccines targeting sperm. Expert Opin Biol Ther 2005; 5(3):381-392; and Sun A. Sperm-based contraceptive vaccines: current status, merits and development. Expert Rev Mol Med 2005; 7(18):1-16).

Figure 2:
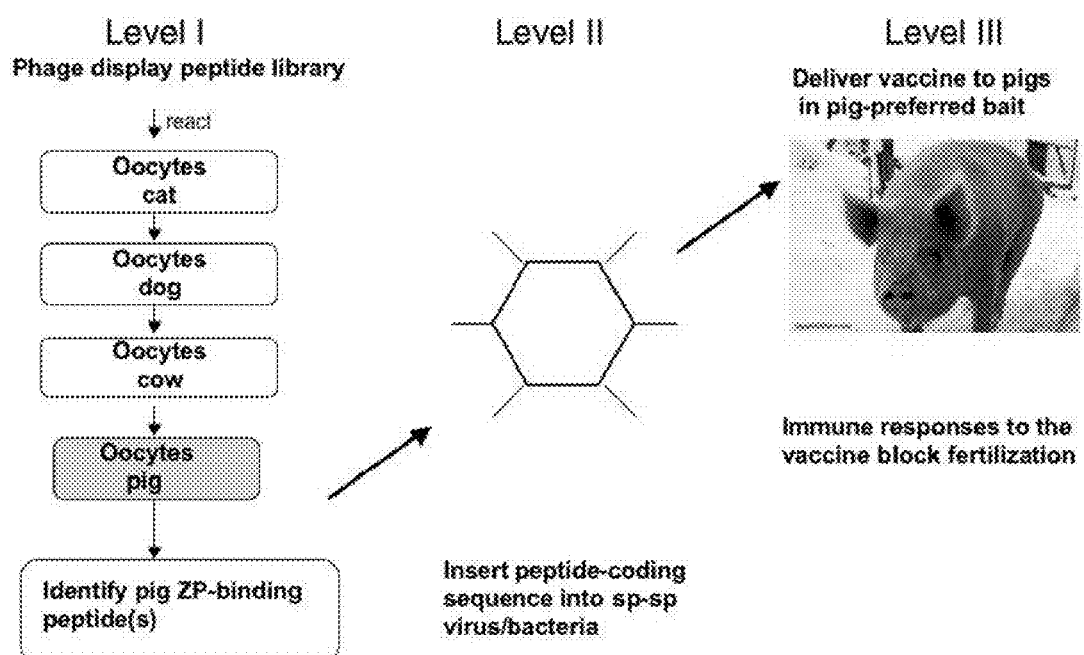
FIG. 2. illustrates a strategy for species-specific overpopulation control for domestic, feral, or wild animals having three major levels of species-specificity (exemplified for swine in this figure).

A strategy was developed for species-specific overpopulation control of domestic, feral, or wild animals having three major levels of species-specificity: Level 1: species-specific antigen, ZP-binding peptide(s) that mimics sperm cell antigens; Level 2: antigen delivery system, for example, species-specific viral or bacterial vector; and Level 3: species-preferred bait and feeder. (See FIG. 2)

Figure 3:
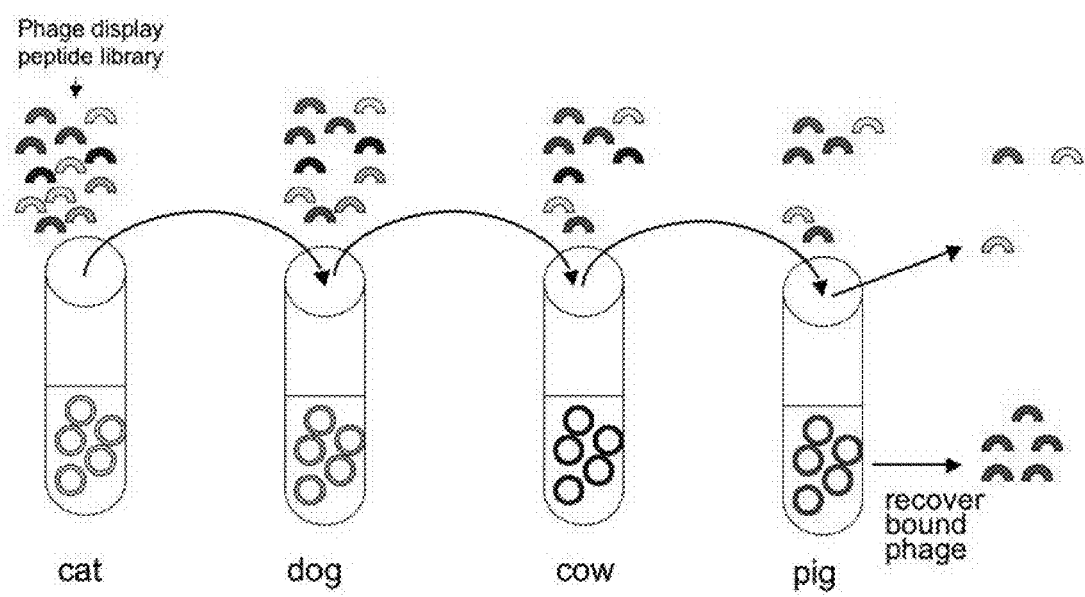
FIG. 3. illustrates selection of species-specific ZP-binding peptides using a phage display library. For the peptides to be species-specific, prior to reaction with oocytes of the target species, a phage display library is reacted with oocytes of non-target species that have close homology with respect to ZP proteins.

For Level 1, species-specific ZP-binding peptides are identified using phage display libraries. (See Samoylova T I, Smith B F. Identification of cell targeting ligands using random peptide-presenting phage libraries. In: Bird C, Smith B F, editors. Genetic Library Construction and Screening: Advanced Techniques and Applications. Heidelberg: Springer-Verlag, 2002: 209-231, the content of which is incorporated by reference in its entirety). Phage display libraries are mixtures of billions of genetically engineered phages which display additional foreign (not of phage origin) peptides on their surfaces. In general, to identify target-binding peptides, a peptide library is first reacted with the target. After that, phage particles not bound to the target are removed by washing steps, and the target-specific phage (bound to the target via displayed peptides) are recovered and amplified. To enrich for the target-specific phage, the whole procedure may be repeated several times (e.g., three or four times). To identify the sequences of the peptides responsible for binding to the target, phage DNAs are isolated, sequenced and translated into peptide sequences. In the approach developed herein, in order to select for peptides that are species-specific, prior to reaction with oocytes of the target species, a phage display library is reacted with oocytes of non-target species that have close homology with respect to ZP glycoproteins. In the example shown in FIG. 3, to select for peptide antigens that are specific for swine, subtractive selection steps on ZP proteins from species of animals with close homology were performed prior to selection steps on ZP of porcine oocytes. These species of animals with close homology included cat, dog and cow. (See Conner S J, Lefievre L, Hughes D C, Barratt C L. Cracking the egg: increased complexity in the zona pellucida. Hum Reprod 2005; 20(5):1148-1152). These subtractive steps remove phage that bind to ZP on oocytes of non-target species, including those that are common to the target and non-target species. Subtractive selection steps on oocytes from non-target species are followed by selection of species-specific phage binding to ZP on porcine oocytes.

For Level 2, oligonucleotide sequences coding for species-specific ZP-binding peptide antigens are inserted into species-specific viral vectors, bacterial vectors, or other vectors. Here, the vector is a delivery mechanism that is used to transfer specific genetic material (oligonucleotide coding a peptide antigen) into host cells. As the result, cells that are transfected with the specific genetic material express the desired peptide which then stimulates an immune response. In addition, immune enhancers may be included in the formulation to improve immunogenicity. Examples of species-specific biological delivery vectors that could be appropriate delivery systems for domestic, feral, or wild swine include porcine-specific adenoviruses (see Hammond J M, Johnson M A. Porcine adenovirus as a delivery system for swine vaccines and immunotherapeutics. Vet J. 2005 January; 169 (1):17-27) and strains of *Salmonella* sp. mostly restricted to infecting swine.

For Level 3, the vector vaccine is incorporated into species-preferred bait. The composition of the bait is specifically formulated for the target species (e.g., feral swine). As an animal contacts, smells, and eats the bait, it becomes immunized and the immune response to the vaccine blocks fertilization. Additionally, the bait can be distributed in feeders designed to exclude species other than the target species.

Example 1

Identification of Peptides that Bind Pig Oocyte ZP

Peptides that bind to ZP glycoproteins on intact pig oocytes were identified using PhD-12 Phage Display Peptide Library purchased from New England BioLabs. The utilized approach selected peptides that mimic the sperm antigen at the level of the ZP-sperm binding. For Experiment 1, three rounds of selection were performed on pig oocytes. (See FIG. 4.) Pig oocytes and oocytes of non-target species (i.e., cat, dog, and cow oocytes as utilized in Example 2) were obtained utilizing a modification of the method disclosed by Dunbar et al. (Biol. Reprod. 1980; 22:941-954). In the first selection round, an aliquot of the primary library was diluted in a blocking buffer and incubated with 1000 intact pig oocytes surrounded by ZP. After incubation, phage expressing peptides not bound to ZP were washed away and the bound phage were recovered by incubation with a lysis buffer. Two additional selection rounds were performed similarly. Translation of foreign oligonucleotide inserts in phage DNA revealed sequences of the peptides that were responsible for binding to pig oocyte ZP. Peptide sequences from the phage display selection on intact pig oocytes surrounded by ZP are shown in FIG. 5. These peptide sequences which bind to pig oocyte ZP may or may not be species-specific. For example, these identified peptide sequence may bind to conservative regions of ZP glycoproteins that are common to multiple species of animals.

Example 2

Identification of Peptides that Bind Specifically to Pig Oocyte ZP

Figure 4:
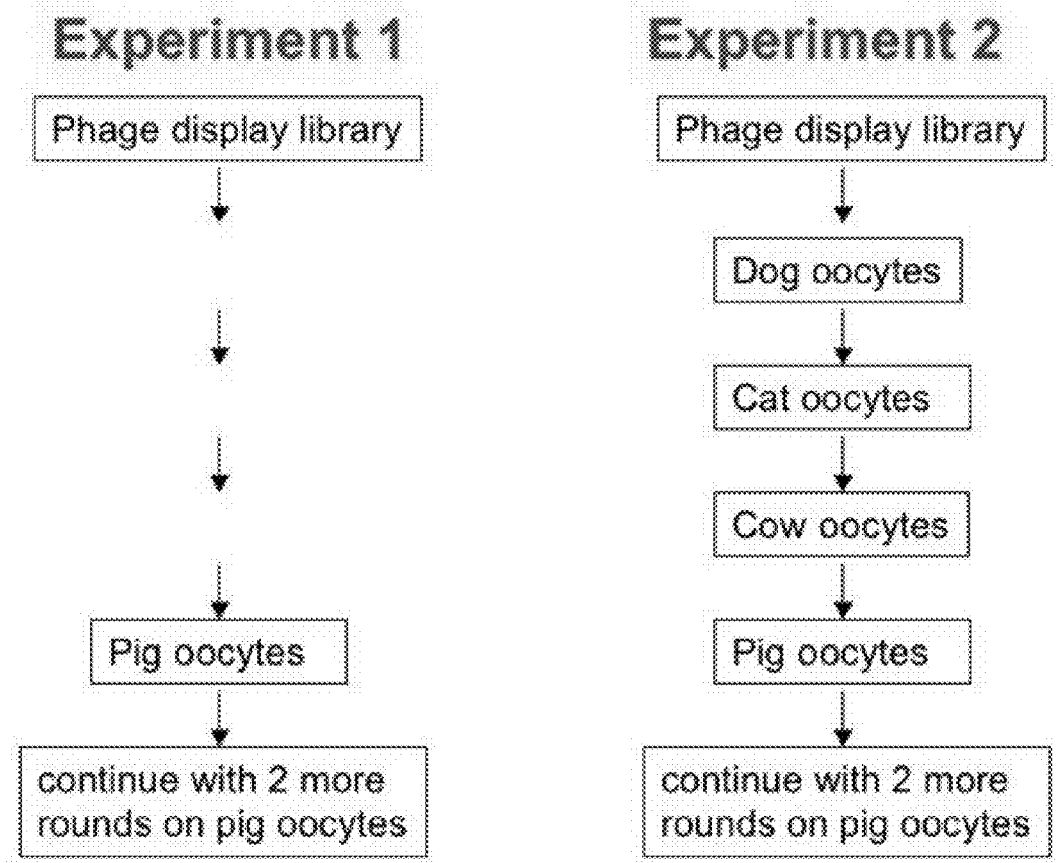
FIG. 4. provides schematics of the experiments described in Examples 1 and 2.

Experiment 2 was designed to identify peptides that bind only to ZP proteins on pig oocytes (pig-specific peptides). (See FIG. 4.) Prior to reaction with pig oocytes, PhD-12 Phage Display Peptide Library was reacted with oocytes of non-target species (cat, dog, and cow oocytes) that have close homology to pig oocytes with respect to ZP proteins. (See Conner S J, Lefievre L, Hughes D C, Barratt C L. Cracking the egg: increased complexity in the zona pellucida. Hum Reprod 2005; 20(5):1148-1152). For each of these subtractive selection steps, 2000 oocytes with ZP from each non-target species were used. Subtractive selection steps were followed by three rounds of selection on pig oocytes (1000 oocytes per round). In each round, phage expressing peptides not bound to ZP of oocytes were washed away and the bound phage were recovered by incubation with lysis buffer. Translation of foreign oligonucleotide inserts in phage DNA revealed sequences of the peptides that were responsible for binding specifically to ZP proteins on pig oocytes. Peptide sequences from phage display selection on intact pig oocytes surrounded by ZP are shown in FIG. 6. Peptide sequences identified in Experiment 2 are pig-specific. Comparative analysis indicates that peptide sequences shown in FIGS. 5 and 6 are different (with the exception of the peptide of SEQ ID NO:2), indicating that peptides common for dog, cat, cow and swine were removed in pre-selection procedures on dog, cat and cow oocytes prior to the three rounds of selection on pig oocytes.

Example 3

Bait Compositions that Target Feral Pigs

Polypeptides comprising or consisting of the peptides of Example 2 may be formulated as species-specific bait compositions that target feral pigs. Alternatively, polynucleotides encoding the peptides identified in Example 2 may be formulated as species-specific bait compositions that target feral pigs. Optionally, the polynucleotides may be inserted in species-specific viral vectors or bacterial vectors for targeting feral pigs, which subsequently are formulated as species-specific bait compositions that target feral pigs.

The bait composition is formulated to attract feral pigs and is formulated not to attract non-target species of animals (e.g., birds). The bait composition may be flavored, colored, or scented, in order to selectively attract feral pigs while not attracting or only minimally attracting a non-target species of animal (e.g., birds or other non-target species). Ingredients that may be used in the bait composition may include, but are not limited to, cereals or grains (e.g., barley), fish (or fish flavoring), meat (or meat flavoring), vegetables (e.g., potatoes), fruits (e.g., apples), dairy products (e.g. milk or milk powder), and oils (e.g., vegetable oil or fish oil).

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention. In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group. Citations to a number of patent and non-patent references are made herein. The cited references are incorporated by reference herein in their entireties.

---

We claim:

1. A method for identifying a peptide that binds specifically to oocytes of a target species of animal in a species-specific manner, the method comprising:
   (a) isolating oocytes of the target species of animal and isolating oocytes of one or more non-target species of animals;
   (b) contacting the isolated oocytes of the target species with a phage library;
   (c) selecting phage from the library that bind specifically to the oocytes of the target species of animal;
   wherein the phage library is first contacted with the oocytes of the one of more non-target species of animals, and subsequently, members of the phage library that do not bind to the oocytes of the one of more non-target species of animals are contacted with the oocytes of the target species of animal and those members of the phage library that bind to the oocytes of the target species of animal are selected, thereby identifying peptides that bind specifically to the oocytes of the target species of animal in a species-specific manner.

2. The method of claim 1, wherein the target species of animal is a swine.

3. The method of claim 1, wherein the non-target species of animals include one or more of felines, canines, and bovines.

4. The method of claim 1, wherein the phage library is contacted with less than 1000 intact oocytes.

5. The method of claim 4, wherein the intact oocytes comprise a zona pellucida.

6. The method of claim 1, wherein selecting phage that bind to the oocytes comprises recovering bound phage by lysing the intact oocytes.

7. The method of claim 1, wherein the method comprises four rounds of contacting and selecting.

8. The method of claim 1, wherein the phage library comprises phage expressing a heterologous peptide of no more than about 7 amino acids.

9. The method of claim 1, wherein the phage library comprises phage expressing a heterologous peptide of no more than about 12 amino acids.

* * * * *

SEQUENCE LISTING

```
<160> NUMBER OF SEQ ID NOS: 26

<210> SEQ ID NO 1
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 1

Asp Ala Asp Asp Gln Thr His Arg Arg Phe Ser Met
1               5                   10

<210> SEQ ID NO 2
<211> LENGTH: 12
```

```
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 2

Asp Ala Asn Arg Leu Pro His Pro Ala Asn Ile Asn
1               5                   10

<210> SEQ ID NO 3
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 3

Asp Leu Asn Gly His Lys Thr Leu Pro Val Ser Lys
1               5                   10

<210> SEQ ID NO 4
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 4

Asn Ile Gly Leu Pro His Asp Leu His Lys Arg Leu
1               5                   10

<210> SEQ ID NO 5
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 5

Gly Leu His Asn Asn Leu His Ala Thr Thr Pro Glu
1               5                   10

<210> SEQ ID NO 6
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 6

Gln Ser Ala Ala Trp Tyr Pro Trp Ser Ala Asp His
```

```
<210> SEQ ID NO 7
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 7

Tyr Thr Val Ser Met Pro Asn Val Lys Asp Ala Ala
1               5                   10

<210> SEQ ID NO 8
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 8

Tyr Met Pro Asn Pro Phe Thr Ala Ser Lys Trp Lys
1               5                   10

<210> SEQ ID NO 9
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 9

Gly Gln Ile Met Pro Leu Pro Thr Asn Leu Leu Val
1               5                   10

<210> SEQ ID NO 10
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 10

Ser Thr Thr Leu Pro Met Gly Ser Asn Ala His Leu
1               5                   10

<210> SEQ ID NO 11
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
```

```
<222> LOCATION: (1)..(12)

<400> SEQUENCE: 11

Thr Tyr Leu Lys Ala Asp Ser Leu Phe Ser Arg Val
1               5                   10

<210> SEQ ID NO 12
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (6)..(6)
<223> OTHER INFORMATION: "Xaa" in position #4 is a naturally occurring
      amino acid
<220> FEATURE:
<221> NAME/KEY: Variable
<222> LOCATION: (8)..(8)
<223> OTHER INFORMATION: "Xaa" in position #4 is a naturally occurring
      amino acid
<220> FEATURE:
<221> NAME/KEY: Variable
<222> LOCATION: (9)..(9)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid

<400> SEQUENCE: 12

Thr Thr Leu Xaa Thr Xaa Ser Xaa Xaa His Xaa Xaa
1               5                   10

<210> SEQ ID NO 13
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (2)..(2)
<223> OTHER INFORMATION: "Xaa" in position #4 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
```

```
<220> FEATURE:
<221> NAME/KEY: Variable
<222> LOCATION: (8)..(8)
<223> OTHER INFORMATION: "Xaa" in position #4 is a naturally occurring
      amino acid
<220> FEATURE:
<221> NAME/KEY: Variable
<222> LOCATION: (9)..(9)
<223> OTHER INFORMATION: "Xaa" in position #4 is a naturally occurring
      amino acid
<220> FEATURE:
<221> NAME/KEY: Variable
<222> LOCATION: (10)..(10)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid

<400> SEQUENCE: 13

Asp Xaa Asn Xaa Leu Pro His Xaa Xaa Xaa Xaa Xaa
1               5                   10

<210> SEQ ID NO 14
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (1)..(1)
<223> OTHER INFORMATION: "Xaa" in position #4 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #4 is a naturally occurring
      amino acid
<220> FEATURE:
<221> NAME/KEY: Variable
<222> LOCATION: (6)..(6)
<223> OTHER INFORMATION: "Xaa" in position #4 is a naturally occurring
      amino acid
<220> FEATURE:
<221> NAME/KEY: Variable
<222> LOCATION: (9)..(9)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (11)..(11)
```

-continued

<223> OTHER INFORMATION: "Xaa" in position #4 is a naturally occurring
      amino acid

<400> SEQUENCE: 14

Xaa Gly Leu Xaa Xaa Xaa Leu His Xaa Thr Xaa Pro
1               5                   10

<210> SEQ ID NO 15
<211> LENGTH: 11
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(11)
<220> FEATURE:
<221> NAME/KEY: Oligopeptide
<222> LOCATION: (1)..(1)
<223> OTHER INFORMATION: "Xaa" in position #4 is a naturally occurring
      amino acid
<220> FEATURE:
<221> NAME/KEY: Oligopeptide
<222> LOCATION: (2)..(2)
<223> OTHER INFORMATION: "Xaa" in position #4 is a naturally occurring
      amino acid
<220> FEATURE:
<221> NAME/KEY: Oligopeptide
<222> LOCATION: (8)..(8)
<223> OTHER INFORMATION: "Xaa" in position #4 is a naturally occurring
      amino acid
<220> FEATURE:
<221> NAME/KEY: Oligopeptide
<222> LOCATION: (9)..(9)
<223> OTHER INFORMATION: "Xaa" in position #4 is a naturally occurring
      amino acid
<220> FEATURE:
<221> NAME/KEY: Oligopeptide
<222> LOCATION: (10)..(10)
<223> OTHER INFORMATION: "Xaa" in position #4 is a naturally occurring
      amino acid
<220> FEATURE:
<221> NAME/KEY: Oligopeptide
<222> LOCATION: (10)..(10)
<223> OTHER INFORMATION: "Xaa" in position #4 is a naturally occurring
      amino acid

<400> SEQUENCE: 15

Xaa Xaa Met Pro Asn Pro Val Xaa Xaa Ala Xaa
1               5                   10

<210> SEQ ID NO 16
<211> LENGTH: 11
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(11)
<220> FEATURE:
<221> NAME/KEY: Variable
<222> LOCATION: (1)..(1)
<223> OTHER INFORMATION: "Xaa" in position #4 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #4 is a naturally occurring

```
        amino acid
<220> FEATURE:
<221> NAME/KEY: Variable
<222> LOCATION: (9)..(9)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid

<400> SEQUENCE: 16

Xaa Gly Ser Xaa Xaa Thr Leu Pro Xaa Ser Xaa
1               5                   10

<210> SEQ ID NO 17
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (2)..(2)
<223> OTHER INFORMATION: "Xaa" in position #4 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #4 is a naturally occurring
      amino acid
<220> FEATURE:
<221> NAME/KEY: Variable
<222> LOCATION: (6)..(6)
<223> OTHER INFORMATION: "Xaa" in position #4 is a naturally occurring
      amino acid
<220> FEATURE:
<221> NAME/KEY: Variable
<222> LOCATION: (9)..(9)
<223> OTHER INFORMATION: "Xaa" in position #4 is a naturally occurring
      amino acid
<220> FEATURE:
<221> NAME/KEY: Variable
<222> LOCATION: (10)..(10)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid

<400> SEQUENCE: 17
```

```
Gln Xaa Ala Xaa Xaa Xaa Pro Trp Xaa Xaa Xaa Xaa
1               5                   10

<210> SEQ ID NO 18
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 18

Thr Leu Gly Trp Thr Ala Asn Glu Ala Pro Arg Arg
1               5                   10

<210> SEQ ID NO 19
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 19

Leu Leu Ala Asp Thr Thr His His Arg Pro Trp Thr
1               5                   10

<210> SEQ ID NO 20
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 20

Ser Gln Ser Pro Ala Met Tyr Ser Pro Thr Arg Pro
1               5                   10

<210> SEQ ID NO 21
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
<220> FEATURE:
<221> NAME/KEY: Oligopeptide
<222> LOCATION: (1)..(12)

<400> SEQUENCE: 21

Ala Val Thr Gln His Leu Lys Phe Lys Gly Phe Asn
1               5                   10

<210> SEQ ID NO 22
<211> LENGTH: 12
<212> TYPE: PRT
<213> ORGANISM: Artificial
<220> FEATURE:
<223> OTHER INFORMATION: Dodecapeptide sequence obtained from M13 minor
      coat protein pIII phage display library
```

```
<220> FEATURE:
<221> NAME/KEY: Oligopeptide
<222> LOCATION: (1)..(12)

<400> SEQUENCE: 22

Ala Asn Phe Asn Met Thr His His Gln Gly His Lys
1               5                   10

<210> SEQ ID NO 23
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (1)..(1)
<223> OTHER INFORMATION: "Xaa" in position #4 is a naturally occurring
      amino acid
<220> FEATURE:
<221> NAME/KEY: Variable
<222> LOCATION: (2)..(2)
<223> OTHER INFORMATION: "Xaa" in position #4 is a naturally occurring
      amino acid
<220> FEATURE:
<221> NAME/KEY: Variable
<222> LOCATION: (7)..(7)
<223> OTHER INFORMATION: "Xaa" in position #4 is a naturally occurring
      amino acid
<220> FEATURE:
<221> NAME/KEY: Variable
<222> LOCATION: (8)..(8)
<223> OTHER INFORMATION: "Xaa" in position #4 is a naturally occurring
      amino acid
<220> FEATURE:
<221> NAME/KEY: Variable
<222> LOCATION: (9)..(9)
<223> OTHER INFORMATION: "Xaa" in position #4 is a naturally occurring
      amino acid
<220> FEATURE:
<221> NAME/KEY: Variable
<222> LOCATION: (10)..(10)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid

<400> SEQUENCE: 23

Xaa Xaa Thr Thr His His Xaa Xaa Xaa Xaa Xaa Xaa
1               5                   10

<210> SEQ ID NO 24
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
```

```
<221> NAME/KEY: Oligopeptide
<222> LOCATION: (1)..(12)
<220> FEATURE:
<221> NAME/KEY: Variable
<222> LOCATION: (1)..(1)
<223> OTHER INFORMATION: "Xaa" in position #4 is a naturally occurring
      amino acid
<220> FEATURE:
<221> NAME/KEY: Variable
<222> LOCATION: (2)..(2)
<223> OTHER INFORMATION: "Xaa" in position #4 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #4 is a naturally occurring
      amino acid
<220> FEATURE:
<221> NAME/KEY: Variable
<222> LOCATION: (7)..(7)
<223> OTHER INFORMATION: "Xaa" in position #4 is a naturally occurring
      amino acid
<220> FEATURE:
<221> NAME/KEY: Variable
<222> LOCATION: (8)..(8)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid

<400> SEQUENCE: 24

Xaa Xaa Asn Xaa Xaa Leu Xaa Xaa Pro Ala Xaa Xaa
1               5                   10

<210> SEQ ID NO 25
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (1)..(1)
<223> OTHER INFORMATION: "Xaa" in position #4 is a naturally occurring
      amino acid
<220> FEATURE:
<221> NAME/KEY: Variable
<222> LOCATION: (2)..(2)
<223> OTHER INFORMATION: "Xaa" in position #4 is a naturally occurring
      amino acid
<220> FEATURE:
<221> NAME/KEY: Variable
<222> LOCATION: (4)..(4)
<223> OTHER INFORMATION: "Xaa" in position #4 is a naturally occurring
      amino acid
<220> FEATURE:
```

```
<221> NAME/KEY: Variable
<222> LOCATION: (5)..(5)
<223> OTHER INFORMATION: "Xaa" in position #4 is a naturally occurring
      amino acid
<220> FEATURE:
<221> NAME/KEY: Variable
<222> LOCATION: (6)..(6)
<223> OTHER INFORMATION: "Xaa" in position #4 is a naturally occurring
      amino acid
<220> FEATURE:
<221> NAME/KEY: Variable
<222> LOCATION: (7)..(7)
<223> OTHER INFORMATION: "Xaa" in position #4 is a naturally occurring
      amino acid
<220> FEATURE:
<221> NAME/KEY: Variable
<222> LOCATION: (8)..(8)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
      amino acid

<400> SEQUENCE: 25

Xaa Xaa Ala Xaa Xaa Xaa Xaa Xaa Arg Pro Xaa Xaa
1               5                   10

<210> SEQ ID NO 26
<211> LENGTH: 12
<212> TYPE: PRT
<213> ORGANISM: Artificial
<220> FEATURE:
<223> OTHER INFORMATION: Consensus motif of dodecapeptide sequences
      obtained from M13 minor coat protein pIII phage display library
<220> FEATURE:
<221> NAME/KEY: Oligopeptide
<222> LOCATION: (1)..(12)
<220> FEATURE:
<221> NAME/KEY: Variable
<222> LOCATION: (1)..(1)
<223> OTHER INFORMATION: "Xaa" in position #4 is a naturally occurring
      amino acid
<220> FEATURE:
<221> NAME/KEY: Variable
<222> LOCATION: (2)..(2)
<223> OTHER INFORMATION: "Xaa" in position #4 is a naturally occurring
      amino acid
<220> FEATURE:
<221> NAME/KEY: Variable
<222> LOCATION: (5)..(5)
<223> OTHER INFORMATION: "Xaa" in position #4 is a naturally occurring
      amino acid
<220> FEATURE:
<221> NAME/KEY: Variable
<222> LOCATION: (6)..(6)
<223> OTHER INFORMATION: "Xaa" in position #4 is a naturally occurring
      amino acid
<220> FEATURE:
<221> NAME/KEY: Variable
<222> LOCATION: (10)..(10)
<223> OTHER INFORMATION: "Xaa" in position #4 is a naturally occurring
      amino acid
<220> FEATURE:
<221> NAME/KEY: Variable
<222> LOCATION: (11)..(11)
<223> OTHER INFORMATION: "Xaa" in position #4 is a naturally occurring
      amino acid
<220> FEATURE:
<221> NAME/KEY: Variable
<222> LOCATION: (12)..(12)
<223> OTHER INFORMATION: "Xaa" in position #4 is a naturally occurring
```

```
amino acid

<400> SEQUENCE: 26

Xaa Xaa Ser Ser Xaa Xaa Ser Ala Ser Xaa Xaa Xaa
1               5                   10
```